United States Patent [19]

Weissman

[11] 4,355,979

[45] * Oct. 26, 1982

[54] LINGUAL DENTAL SPLINT DEVICE

[75] Inventor: Bernard Weissman, New York, N.Y.

[73] Assignee: Ipco Corporation, White Plains, N.Y.

[*] Notice: The portion of the term of this patent subsequent to Apr. 14, 1998, has been disclaimed.

[21] Appl. No.: 188,356

[22] Filed: Sep. 18, 1980

Related U.S. Application Data

[63] Continuation-in-part of Ser. No. 70,247, Aug. 27, 1979, Pat. No. 4,260,383.

[51] Int. Cl.³ .............................................. A61C 5/04
[52] U.S. Cl. .................................................. 433/225
[58] Field of Search .................... 433/174, 173, 225; 428/92; 24/276, 277

[56] References Cited

U.S. PATENT DOCUMENTS

| 3,414,975 | 12/1968 | Small | 433/176 |
| 3,605,214 | 9/1971 | Spotts et al. | 24/277 |

Primary Examiner—Robert Peshock
Attorney, Agent, or Firm—Friedman, Goodman & Teitelbaum

[57] ABSTRACT

A lingual dental splinting device having an elongated bar-like body member with at least two tubular members extending perpendicularly from one side thereof, the tubular members being received in corresponding holes which respectively extend transversely through adjacent teeth when the body member is disposed in a side wall channel laterally extending between the adjacent teeth, the tubular members including axial openings therethrough. A brace member is disposed in an opposing side wall channel which also laterally extends between the adjacent teeth. A U-shaped wire has its legs passing through or extending from the brace member. The legs extend from the opposing side wall through the axial openings in the tubular members so as to extend from the bar-like body member. Restraining devices are then disposed at the distal ends of the legs so as to hold the body member in place.

8 Claims, 8 Drawing Figures

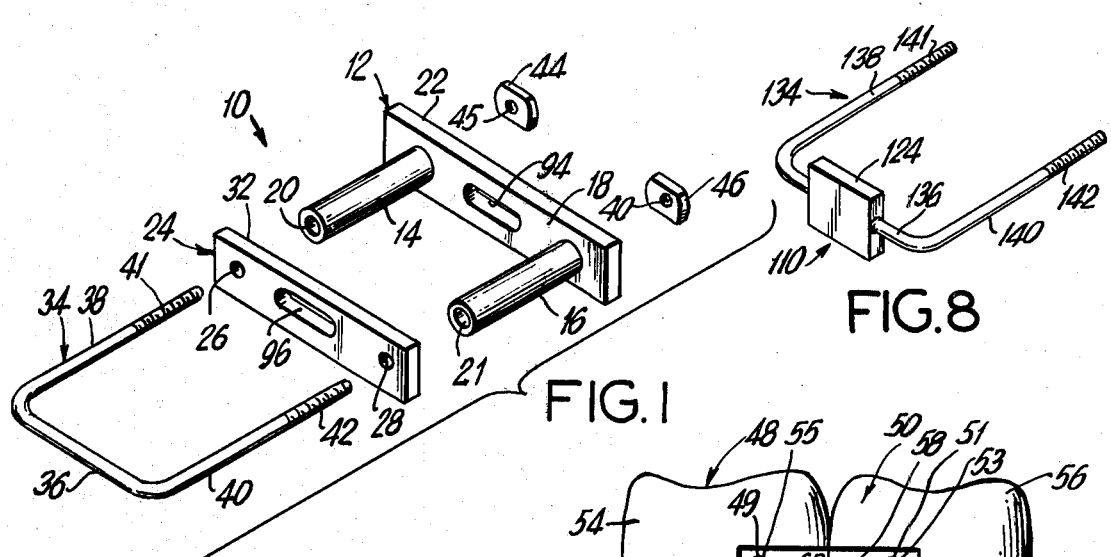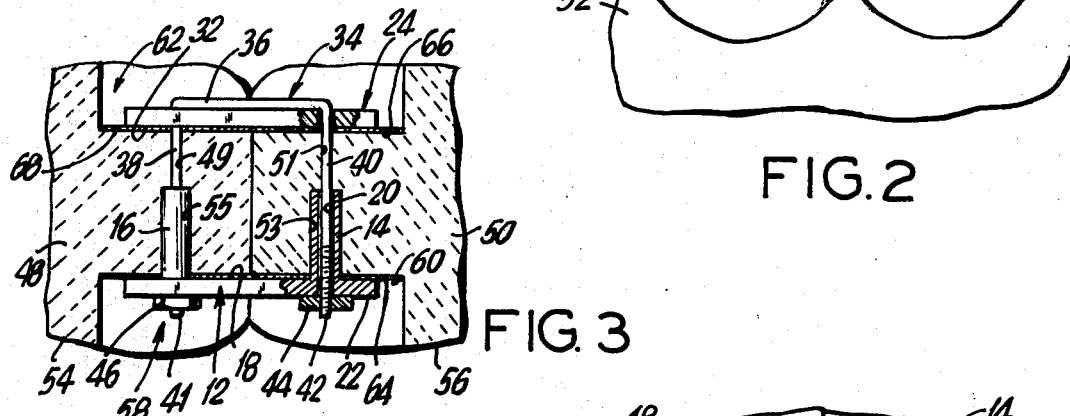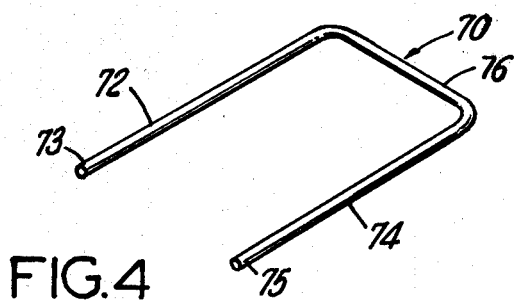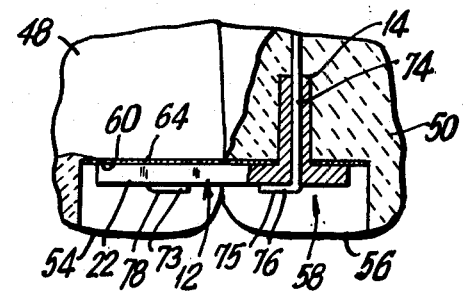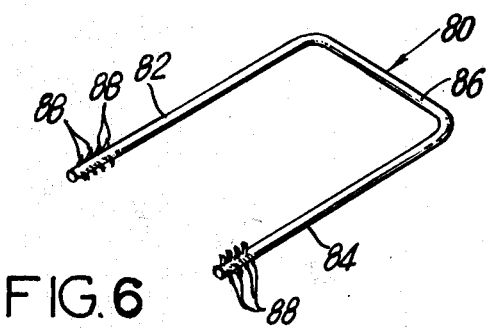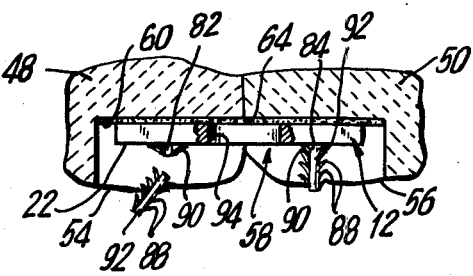

LINGUAL DENTAL SPLINT DEVICE

RELATIONSHIP TO OTHER APPLICATIONS

This application is a continuation-in-part application of Ser. No. 070,247 filed Aug. 27, 1979, now U.S. Pat. No. 4,260,383 for a "Dental Retaining Splint".

BACKGROUND OF THE INVENTION

This invention relates to dentistry in general, and more particularly to a dental splinting device for the reinforcement of dentition and especially to a lingual splinting device.

The use of dental splints has been a highly specialized field of dentistry. The splints themselves have also presented serious limitations, such as the requirement that the securing pins for the splint must be disposed in horizontal parallelism, the need for involved and complicated procedures in the preparation of the teeth and the utilization of special equipment in order to assure the proper positioning and placement of the splint in the teeth.

An improved dental retaining splint which avoids such problems was presented in the aforementioned copending parent application. Such application describes a dental retaining splint having an elongated bar-like member with a number of tubular members extending therefrom. The tubular members have axial openings extending therethrough. In utilizing the splint, it is first temporarily held in a channel formed in adjacent teeth with the tubular member extending upwardly from the teeth. The tubular members have axial openings therethrough and these openings are utilized as guides for a drill in order to form pilot holes in the teeth. The splint is then removed and the pilot holes function as lead holes for the formation of enlarged bores to receive the tubular members therein. The splint is then replaced so that the tubular members are now disposed downwardly into the bores formed therefor. An inlay fills the channel and covers the splint as the final procedural step.

While such improved dental retaining splint provides greater use and easier installation, the splint described is of a type which must be vertically inserted into the teeth and provides for reinforcement of the teeth by means of its positioning across the occlusal surface of the teeth. Frequently, however, it is not the best procedure to place the retaining splint along the occlusal surfaces. For example, in many cases the occlusal surfaces of the adjacent teeth may be deformed, damaged, or otherwise unfit for supporting the retaining splint. At other times, the relative height of adjacent teeth is so varied that the lateral positioning of the retaining splint across such adjacent teeth would be awkward and would not be readily accomplished. At other times, the position of the teeth may be such so that it is awkward to provide the vertical bores in the teeth in order to support the aforedescribed retaining splint.

It would accordingly be desirable to provide a dental splinting device which utilizes the concept of the aforementioned dental retaining splint but which could be utilized in a horizontal position, whereby it is lingually placed into the side wall of adjacent teeth and is secured to the teeth so as to provide suitable reinforcement of adjacent teeth.

SUMMARY OF THE INVENTION

Accordingly, it is an object of the present invention to provide a dental splinting device of the type described in the aforementioned parent application and which can be utilized in a horizontal position.

Another object of the present invention is to provide a dental splinting device which may be readily secured for the reinforcement and retention of dentition in the mouth and which can be utilized in a horizontal lingual position between adjacent teeth.

Still another object of the present invention is to provide a dental splinting device which can be placed in a horizontal channel positioned in the side wall of adjacent teeth and which can be clamped by means of a clamping device positioned on the other side of the teeth.

Yet another object of the present invention is to provide a dental splinting device which includes a first member placed on the buccal surfaces of adjacent teeth and a second member placed on the lingual surfaces of the adjacent teeth, and clamping means for securing the members together.

Still another object of the present invention is to provide a lingual dental splinting device which may be fabricated in a simple, efficient and economical manner and can be utilized in simplified procedures.

In accordance with the present invention, there is provided a dental splinting device formed of an elongated barlike body member having at least two tubular members extending perpendicularly from one side thereof. The tubular members are received in corresponding holes which respectively extend horizontally transversely through adjacent teeth while the body member is disposable in a side wall channel laterally extending between the adjacent teeth. The tubular members include axial openings which extend therethrough. A clamping device is disposable in an opposing side wall channel which laterally extends between the adjacent teeth. The clamping device passes through the transverse holes in the teeth and into the axial openings, and serves to secure the elongated body member in the adjacent teeth.

The clamping device includes a brace of a configuration substantially similar to the body member and which includes openings through which the legs of a U-shaped wire can pass while the bight portion of the wire is positioned transversely across the brace. The legs of the wire extend from the opposing side of the teeth through the axial openings of the tubular members to the other side of the elongated bar member with the brace being positioned in the opposing side wall channel. A restraining device at the distal ends of the legs of the wire holds the body member firmly in place in the adjacent teeth. In a modified construction of the clamping device, the brace and the U-shaped wire are integrally formed as a one piece member with the brace portion disposed on the bight of the U-shaped wire.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is a perspective exploded view illustrating the dental splinting device in accordance with the present invention;

FIG. 2 is an elevational view illustrating the formation of a channel and holes in adjacent teeth, for receiving the dental splinting device of the present invention;

FIG. 3 is a cross sectional plan view of the adjacent teeth, with parts broken away, illustrating the positioning and securing of the dental splinting device in the channel provided therefor;

FIG. 4 is a perspective view of another embodiment of the U-shaped clamping wire device;

FIG. 5 is a partially broken away, cross sectional plan view of the adjacent teeth illustrating the securing of the clamping wire device shown in FIG. 4;

FIG. 6 is a perspective view of a further embodiment of the U-shaped clamping wire device;

FIG. 7 is a partially broken away, cross sectional plan view of the adjacent teeth and illustrating the securing of the clamping wire device shown in FIG. 6; and FIG. 8 is a perspective view of another embodiment of the U-shaped clamping wire device having a brace portion thereon.

In the various figures of the drawing, like reference characters designate like parts.

DETAILED DESCRIPTION OF THE PREFERRED EMBODIMENT

Referring now to FIG. 1, the dental splinting device of the present invention is shown generally at 10 and comprises a bar-like body member 12 of substantially rectangular configuration having two tubular members 14, 16, extending perpendicularly outwardly from one side surface 18 thereof. Each of the tubular members include axial openings 20, 21 extending entirely therethrough, and through the body member 12 so that the openings are available from the opposing surface 22 of the body member 12.

The dental splinting device also includes a brace member 24 also formed of substantially rectangular configuration and being of a size substantially the same as the body member 12. Apertures 26, 28 are formed through the brace member and pass from its one surface 30 entirely through to the opposing surface 32.

A U-shaped wire 34 is also provided which includes a bight section 36 from which extend the two spaced apart legs 38, 40. In the embodiment shown, the distal ends of the legs are threaded at 41, 42.

The apertures 26, 28 in the brace member 24 are of a size to permit passage therethrough of the legs 38, 40, which legs can also pass through the axial openings 20, 21 formed in the tubular members 14, 16 so as to permit the distal ends 41, 42 of the wire to pass outwardly from the opposing surface 22 of the body member 12. The distal ends can then be secured in place by means of the nuts 44, 46 having threaded openings 45, 47 therethrougyn, which thread into the distal ends 41, 42 of the legs thereby clamping the body member 12 in place.

Referring now to FIGS. 2 and 3, the operation of the present inventive device will be described. However, it is noted, that the procedures performed on the lingual and buccal surfaces set forth below are given by way of example, wherein according to the present invention, the splinting device can be reversed relative to the lingual and buccal surfaces whereby the procedure on the lingual surface would be performed on the buccal surface, and accordingly the procedure on the buccal surface would then be performed on the lingual surface.

FIG. 2 shows adjacent teeth 48, 50 extending from the gum surface 52 therebelow. The lingual surfaces of the teeth 54, 56 are shown, in which there is formed a horizontal channel 58 extending laterally across the adjacent teeth and partially into the teeth.

After the channel 58 is formed in the lingual surfaces, a layer of temporary adhesive, such as wax or other suitable material, is disposed on the inward surface 60 of the channel. The body member 12 is then positioned on the adhesive with the tubular members 14, 16 extending outwardly therefrom so that the body member is held by the temporary adhesive. Once the body member is secured in the channel 58, a pilot drill is inserted into the openings 20, 21 of the tubular members 14, 16, and pilot holes 49, 51 are formed extending entirely through the respective teeth so as to extend through the buccal surfaces thereof.

Typically, as shown in FIG. 3, a channel 62 will also be formed in the opposing wall or buccal surfaces of the adjacent teeth. The channel 62 will be commensurate with the channel 58 formed in the lingual surfaces. Accordingly, the pilot holes 49, 51 will be drilled until they reach the channel 62 formed in the buccal surfaces. Preferably, the drill bit utilized to form such pilot holes has a diameter approximately equal to the diameter of the axial openings 20, 21 of the tubular members 14, 16, wherein as set forth above, the tubular members 14, 16 function as drill guides for the drill bit when forming the pilot holes.

After the pilot holes 49, 51 have been made entirely transversely through the teeth extending from the lingual to the buccal surface channels, the splint is removed from the channel 58. Another dental drill is then used to form larger bores 53, 55 in the teeth where the pilot holes previously formed function as lead holes for the larger drill bit in the formation of the larger bores. The drill bit utilized to form the larger bores has a predetermined length proximating the length of the tubular members 14, 16 so that the larger bores 53, 55 will only extend partially through the teeth from channel 58 formed in the lingual surfaces, so as to accommodate the tubular members 14, 16. Thus, the larger sized bores 53, 55 do not extend entirely transversely through the teeth. In order to achieve such partial entry, the larger drill bit can be provided with a stop or abutment which contacts the base 60 of the channel 58 when the desired length of the bores has been reached.

After the pilot holes have been drilled entirely through the teeth, and the larger bores are drilled partially through the teeth, a layer of permanent adhesive 64 is placed on the inner surface 60 of the channel 58 and a corresponding layer of permanent adhesive 66 is placed at the inner surface 68 of the channel 62. The body member 12 is then positioned in the channel 58 with the surface 18 in contact with the permanent adhesive 64 and with the tubular members 14, 16 now positioned in the bores 53, 55 provided transversely in the teeth. The drill bit utilized to form such bores should have a diameter approximately equal to or slightly larger than the outside diameter than the tubular members 14, 16 so that the bores 53, 55 are large enough to receive the tubular members therein, as can best be seen in FIG. 3.

The brace member 24 is then positioned in the opposing channel 62 with the surface 32 secured on the permanent adhesive 66. The apertures 26, 28 in the brace member 24 should be registered with the holes 49, 51 extending entirely through the teeth. In order to facilitate accurate location of the brace member, it is preferable to initially insert the U-shaped member 34 into the brace member so that the legs 38, 40 of the member 34 into the brace member so that the legs 38, 40 of the U-shaped member can be inserted into the holes 49, 51 and utilized to suitably locate the brace member 24 in position in the channel 62.

The legs 38, 40 of the U-shaped wire 34 pass through the holes extending transversely through the teeth and continue into the axial openings 20, 21 in the tubular members 14, 16 and then extend outwardly from the body member 12. The nuts 44, 46 can then be threaded onto the distal ends 41, 42 of the legs 38, 40 of the wire 34 and tightened onto the surface 22 of the body member 12 so as to tighten the body member into place and secure it in its retaining position across the adjacent teeth. An inlay (not shown) can then be placed in both the channels 58 and 62 so as to cover and complete the dental procedure. Such dental inlays are well known in the dentistry art.

Thus, the tubular members 14, 16 function to retain the splint 10 in position to secure one tooth to its adjacent tooth, and the U-shaped clamping wire 34 together with the brace member 24 are utilized to securely hold the body member 12 in a secure position across the adjacent teeth 48, 50.

Referring now to FIGS. 4 and 5, an alternate embodiment of the U-shaped wire and clamping arrangement is shown. As shown in FIG. 4, the U-shaped wire 70 includes the legs 72, 74 and the bight portion 76, wherein the legs 72, 74 are preferably longer than the legs 38, 40 of wire 34. The distal ends 73, 75 of the legs 72, 74 are smooth and unthreaded. As shown in FIG. 5, the legs 72, 74 pass into the openings provided in the teeth and then through the axial openings in the tubular members 14, 16 so that their distal ends 73, 75 protrude past the surface 22 of the body member 12. The distal ends 73, 75 are then bent into an L-shaped configuration 76, 78, so as to lie against the surface 22 of the body member 12 and securely hold it in place. Again, inlay material can be applied as before.

FIGS. 6 and 7 show yet a further embodiment of the U-shaped wire and clamping arrangement. The U-shaped member shown in FIG. 6 as 80 includes the legs 82, 84 interconnected by the bight section 86. A series of longitudinally spaced apart barbs 88 are positioned at the distal ends of each of the legs 82, 84. When the U-shaped wire is inserted into the axial openings and extends outwardly of the body member 12, one of the sets of barbs 88 on each leg, for example the barb set 90 shown in FIG. 7, will include the last barb or barbs to engage onto the rear surface 22 of the body member 12 and will be the particular barb or barbs which tightly secure the body member 12 into place for rigidly connecting the adjacent teeth. The wire end portion 92 beyond the barb 90 can then be cut and eliminated since it serves no retaining purpose. The barbs thus serve to clamp the body member in place and hold it in position in the adjacent teeth. Again inlay material can be used to fill in the channels as heretofore described.

The dental retaining splint 10 of the present invention can be fabricated from a metal material suitable for use in dentistry so that the splint can be compatible for use in the patient's teeth.

As shown in FIG. 1, oval shaped apertures 94, 96 are respectively formed through the mid section, respectively, of the body member 12 and the brace member 24. Such openings are useful for receiving a positioning tool which can suitably place the members in their respective channels, and subsequently, for removal of the members. Additionally, it provides a space, as indicated in FIG. 7, for the inlay material to insure additional retentive strength of the members in their respective channels.

Referring now to FIG. 8, another embodiment of the clamping arrangement is shown generally at 110, comprising an integral one piece construction including a U-shaped wire 134 having a brace portion 124 disposed on the bight section 136 thereof. The distal ends of the wire legs 138, 140 are threaded at 141, 142 respectively. Accordingly, the clamping arrangement 110 replaces the above mentioned brace member 24 and U-shaped wire 34 shown in FIG. 1, and functions in a similar manner thereto so that a further operational description thereof is not thought necessary.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental splinting device comprising:
   an elongated bar-like body member disposable in a side wall channel laterally extending between adjacent teeth;
   retaining means extending outwardly from said body member for being disposed in bores provided transversely in the adjacent teeth through a base wall of the side wall channel, said retaining means positioning said body member against the adjacent teeth when said body member is in a final position in the channel;
   said retaining means including two tubular members extending perpendicularly from said body member for being received in the bores of the adjacent teeth;
   said tubular members including guide means for guiding a drill during formation of a pilot hole through each of the adjacent teeth when said body member is initially positioned in the channel with said tubular members extending outwardly from the base wall of the channel, the pilot holes functioning as lead holes for formation of the bores in the adjacent teeth;
   said guide means including an axial opening extending through each of said tubular members and through said body member;
   clamping means disposable in an opposing side wall channel laterally extending between the adjacent teeth, said clamping means passing through said axial openings of said tubular members and engaging said elongated body member for securing said elongated body member in the adjacent teeth;
   said clamping means including a U-shaped wire having legs respectively extending from the opposing side wall of the teeth through said tubular member axial openings to the other side of said elongated body member, with a bight portion of said wire being disposable in the opposing side wall channel, said legs being provided with restraining means at distal end of each leg of said U-shaped wire for holding said body member firmly in place in the adjacent teeth.

2. A dental splinting device as in claim 1, wherein said distal ends of said legs are externally threaded, and wherein said restraining means includes nuts having threaded openings therein for threadingly receiving the respective distal ends of said legs, said nuts engaging against said elongated body member.

3. A dental splinting device as in claim 1, wherein said restraining means includes L-shaped bends provided at said distal ends of said legs for engaging against said other side of said body member.

4. A dental splinting device as in claim 1, wherein said restraining means includes a series of longitudinally spaced apart barbs at said distal ends of each of said legs, at least one barb on each leg engaging said other side of the body member, with an end portion of said legs beyond said one barb being available for severance.

5. A dental splinting device as in claim 1, and further comprising a brace wire having spaced apart openings for receiving therethrough said legs of said U-shaped member, said brace member being disposable in said opposing side wall channel with said bight portion of said wire positioned against said brace member.

6. A dental splinting device as in claim 5, wherein said brace member and said body member each include an elongated aperture extending therethrough.

7. A dental splinting device as in claim 1, wherein said body member in the side wall channel is disposed on lingual surfaces of the adjacent teeth, and said clamping means in the opposing side wall channel is disposed on buccal surfaces of the adjacent teeth to define a lingual dental splinting device.

8. A dental splinting device as in claim 1, wherein a brace portion is provided on said bight portion of said wire, said brace portion being disposable in said opposing side wall channel.

* * * * *